US00PP27473P3

(12) United States Plant Patent
Oudolf

(10) Patent No.: US PP27,473 P3
(45) Date of Patent: Dec. 20, 2016

(54) ***VERONICA* PLANT NAMED 'CHALLENGER'**

(50) Latin Name: *Veronica virginicum*
Varietal Denomination: Challenger

(71) Applicant: Petrus Hendricus Oudolf, Hummelo (NL)

(72) Inventor: Petrus Hendricus Oudolf, Hummelo (NL)

(73) Assignee: Green Elite Collection B.V., Lisserbroek (NL)

( * ) Notice: Subject to any disclaimer, the term of this patent is extended or adjusted under 35 U.S.C. 154(b) by 59 days.

(21) Appl. No.: 14/545,185

(22) Filed: Apr. 4, 2015

(65) Prior Publication Data

US 2016/0295765 P1 Oct. 6, 2016

(51) Int. Cl.
*A01H 5/02* (2006.01)

(52) U.S. Cl.
USPC ..... Plt./251

(58) Field of Classification Search
USPC ..... Plt./251
See application file for complete search history.

(56) References Cited

PUBLICATIONS

UPOV Plant Breeders' Rights QZ PBR 20140008, published Apr. 15, 2014.*
UPOV Plant Breeders' Right CA PBR 14-8501, published Jan. 31, 2015.*

* cited by examiner

*Primary Examiner* — Anne Grunberg
(74) *Attorney, Agent, or Firm* — C. A. Whealy

(57) ABSTRACT

A new and distinct cultivar of *Veronica* plant named 'Challenger', characterized by its upright and relatively compact plant habit; moderately freely branching habit; freely flowering habit; light purple to white-colored flowers arranged on long racemes; and good garden performance.

3 Drawing Sheets

Botanical designation: *Veronica virginicum.*
Cultivar denomination: 'CHALLENGER'.

BACKGROUND OF THE INVENTION

The present invention relates to a new and distinct *Veronica* plant, botanically known as *Veronica virginicum* and hereinafter referred to by the cultivar name 'Challenger'.

The new *Veronica* plant originated from an open-pollination in July, 2011 in Hummelo, The Netherlands, of *Veronica virginicum* 'Roseum', not patented, as the female, or seed, parent with an unknown selection of *Veronica virginicum* as the male, or pollen, parent. The new *Veronica* plant was discovered and selected by the Inventor as a single flowering plant within the progeny of the stated open-pollination in a controlled environment in Hummelo, The Netherlands in July, 2013.

Asexual reproduction of the new *Veronica* plant by vegetative softwood cuttings in Hummelo, The Netherlands, since the spring of 2014, has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype of the new *Veronica* plant may vary somewhat with variations in environmental conditions such as temperature and light intensity without, however, any variance in genotype.

The following traits have been repeatedly observed and are determined to be the unique characteristics of 'Challenger'. These characteristics in combination distinguish 'Challenger' as a new and distinct *Veronica* plant:

1. Upright and relatively compact plant habit.
2. Moderately freely branching habit.
3. Freely flowering habit.
4. Light purple to white-colored flowers arranged on long racemes.
5. Good garden performance.

Plants of the new *Veronica* differ primarily from plants of the female parent, 'Roseum', in the following characteristics:

1. Plants of the new *Veronica* are shorter and more compact than plants of 'Roseum'.
2. Plants of the new *Veronica* have stronger stems than plants of 'Roseum'.

Plants of the new *Veronica* can be compared to plants of *Veronica spicata* 'Erica', not patented. In side-by-side comparisons conducted by the Inventor in Hummelo, The Netherlands, plants of the new *Veronica* differed from plants of 'Erica' in the following characteristics:

1. Plants of the new *Veronica* were shorter and more compact than plants of 'Erica'.
2. Plants of the new *Veronica* were more freely branching than plants of 'Erica'.
3. Plants of the new *Veronica* and 'Erica' differed in stem color as plants of 'Erica' had darker-colored stems.

BRIEF DESCRIPTION OF THE PHOTOGRAPHS

The accompanying colored photographs illustrate the overall appearance of the new *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Challenger' grown in a container.

The photograph on the second sheet is a close-up view of a typical leaf of 'Challenger'.

The photograph on the third sheet is a close-up view of a typical inflorescence of 'Challenger'.

DETAILED BOTANICAL DESCRIPTION

Plants used for the aforementioned photographs and following description were grown during the late summer in an outdoor nursery in Lisserbroek, The Netherlands and under cultural practices typical of *Veronica* production. During the production of the plants, day temperatures ranged from 15° C. to 25° C. and night temperatures ranged from 8° C. to averaged 18° C. Plants were four months old when the photographs and description were taken. In the following description, color references are made to The Royal Horticultural Society Colour Chart, 2007 Edition, except where general terms of ordinary dictionary significance are used.

Botanical classification: *Veronica virginicum* cultivar Challenger.

Parentage:

*Female, or seed, parent.*—*Veronica virginicum* 'Roseum', not patented.

*Male, or pollen, parent.*—Unknown selection of *Veronica virginicum*, not patented.

Propagation:

*Type cutting.*—Vegetative softwood cuttings.

*Root description.*—Fleshy; medium in thickness; greyed white in color.

*Rooting habit.*—Moderately freely branching; dense.

Plant description:

*Growth and plant habit.*—Upright and relatively compact plant habit; moderately vigorous growth habit; moderately freely branching habit with about four basal branches developing per plant.

*Plant height.*—About 37 cm.

*Plant width.*—About 19.5 cm.

*Lateral branch description.*—Length: About 19 cm. Diameter: About 2 mm. Internode length: About 2.7 cm. Strength: Strong. Texture: Moderately pubescent. Color: Close to 144B to 144C.

Leaf description:

*Arrangement.*—Whorled, simple.

*Length.*—About 6.4 cm.

*Width.*—About 3 cm.

*Shape.*—Ovate.

*Apex.*—Apiculate.

*Base.*—Short attenuate.

*Margin.*—Finely serrate.

*Texture, upper and lower surfaces.*—Smooth, glabrous.

*Luster, upper and lower surfaces.*—Slightly glossy.

*Venation pattern.*—Pinnate.

*Color.*—Developing leaves, upper surface: Slightly darker than 143A. Developing leaves, lower surface: Close to 146B. Fully expanded leaves, upper surface: Close to N137A; venation, close to 144A. Fully expanded leaves, lower surface: Close to 147B; venation, close to 145D.

*Petioles.*—Length: About 3 mm. Diameter: About 2 mm. Texture, upper and lower surfaces: Smooth, glabrous. Color, upper and lower surfaces: Close to 144B.

Flower description:

*Flower shape, arrangement and habit.*—Single campanulate flowers arranged on terminal racemes; flowers face mostly outwardly; freely flowering habit with about 200 flowers developing per inflorescence.

*Fragrance.*—None detected.

*Natural flowering season.*—Flowering continuous from July to late September in The Netherlands.

*Flower longevity on the plant.*—About one week; flowers not persistent.

*Flower buds.*—Length: About 4 mm. Diameter: About 2 mm. Shape: Ovate. Color: Close to 76D; towards the apex, close to 73B to 73C.

*Inflorescence length.*—About 9.8 cm.

*Inflorescence diameter.*—About 1.8 cm.

*Flower diameter.*—About 4 mm by 6 mm.

*Flower depth (height).*—About 6 mm.

*Petals.*—Quantity and arrangement: Four; lower 60% fused towards the base. Length: About 5 mm. Width: About 1.5 mm. Shape: Oblanceolate. Apex: Acute. Margin: Entire. Texture, upper and lower surfaces: Smooth, glabrous. Color: When opening, upper and lower surfaces: Close to 76D. Fully opened, upper and lower surfaces: Close to N155B; at the base of the free part, small dots, close to 75B to 75C; color does not fade with development.

*Sepals.*—Quantity and arrangement: Seven sepals, lower 5% fused towards the base. Length: About 2 mm. Width: About 0.8 mm. Shape: Narrowly ovate. Apex: Acute. Margin: Entire. Texture, upper and lower surfaces: Smooth, glabrous. Color, upper and lower surfaces: Close to 138C.

*Peduncles.*—Length: About 9.5 cm. Diameter: About 2 mm. Strength: Strong. Aspect: Mostly upright. Texture: Smooth, glabrous. Color: Close to 138C.

*Pedicels.*—Length: About 1 mm. Diameter: About 0.5 mm. Strength: Strong. Aspect: About 60° from the peduncle axis. Texture: Smooth, glabrous. Color: Close to 138C.

*Reproductive organs.*—Stamens: Quantity per flower: Two. Filament length: About 5 mm. Filament color: Close to 76B. Anther shape: Elliptic. Anther length: About 1 mm. Anther color: Close to 168C. Pollen amount: Moderate. Pollen color: Close to 12B. Pistils: Quantity per flower: One. Pistil length: About 5 mm. Stigma shape: Clavate. Stigma color: Close to 64A. Style length: About 4.5 mm. Style color: Close to 75A. Ovary color: Close to 146A tinged with close to N77C.

*Seeds and fruits.*—To date, seed and fruit production have not been observed on plants of the new *Veronica*.

Pathogen & pest resistance: Plants of the new *Veronica* have not been noted to be resistant to pathogens and pests common to *Veronica* plants.

Garden performance: Plants of the new *Veronica* have exhibited good garden performance and to be tolerant to rain, wind, high temperatures about 35° C. and to be hardy to USDA Hardiness Zone 4.

It is claimed:

1. A new and distinct *Veronica* plant named 'Challenger' as illustrated and described.

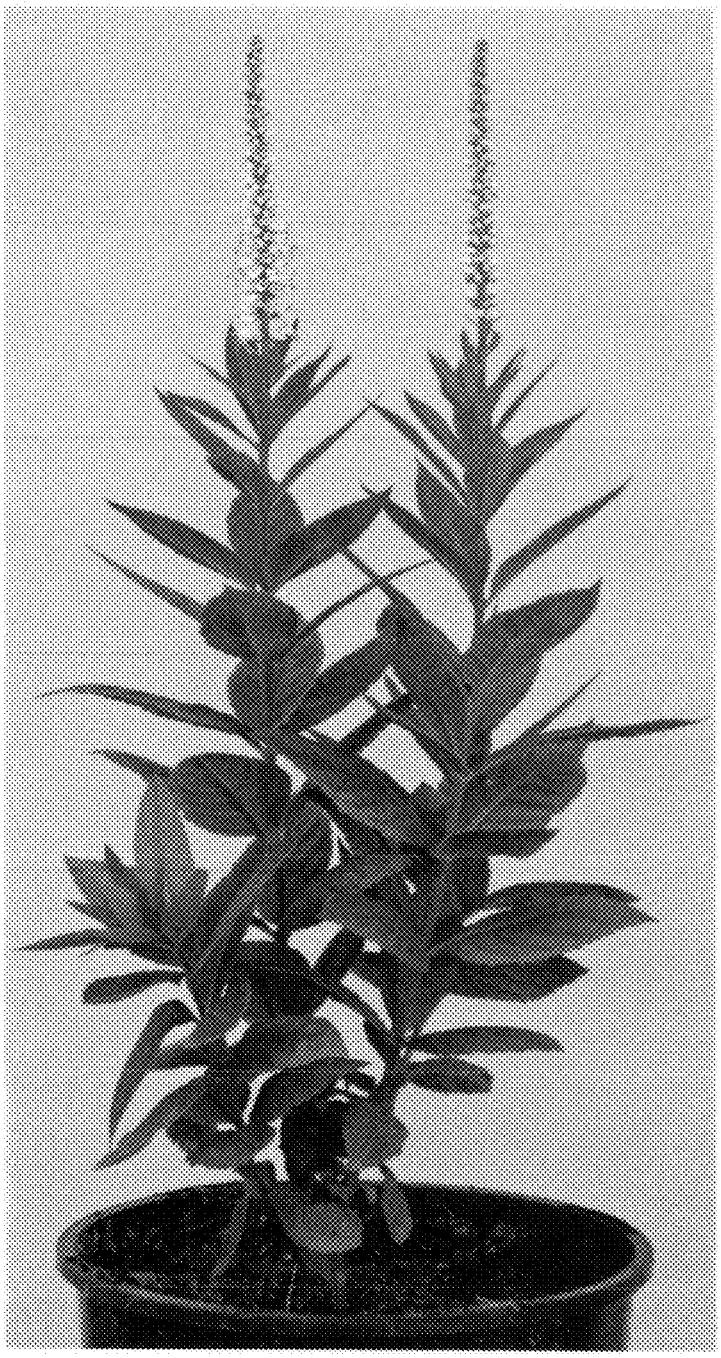

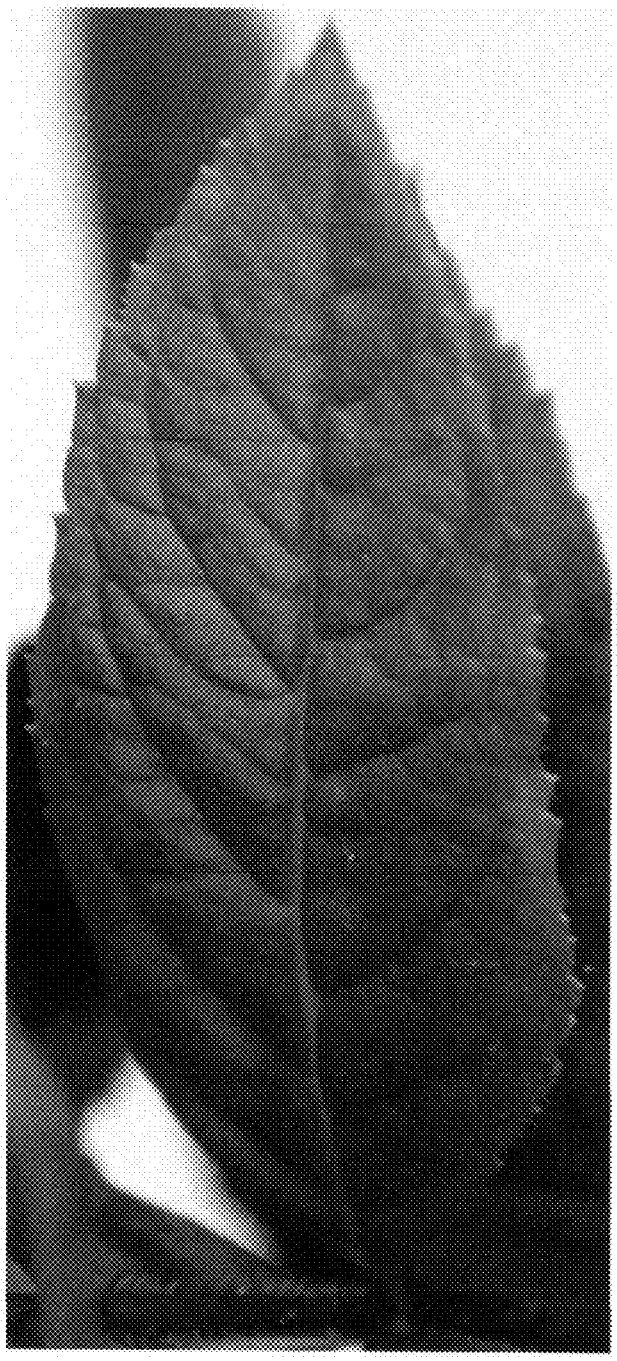

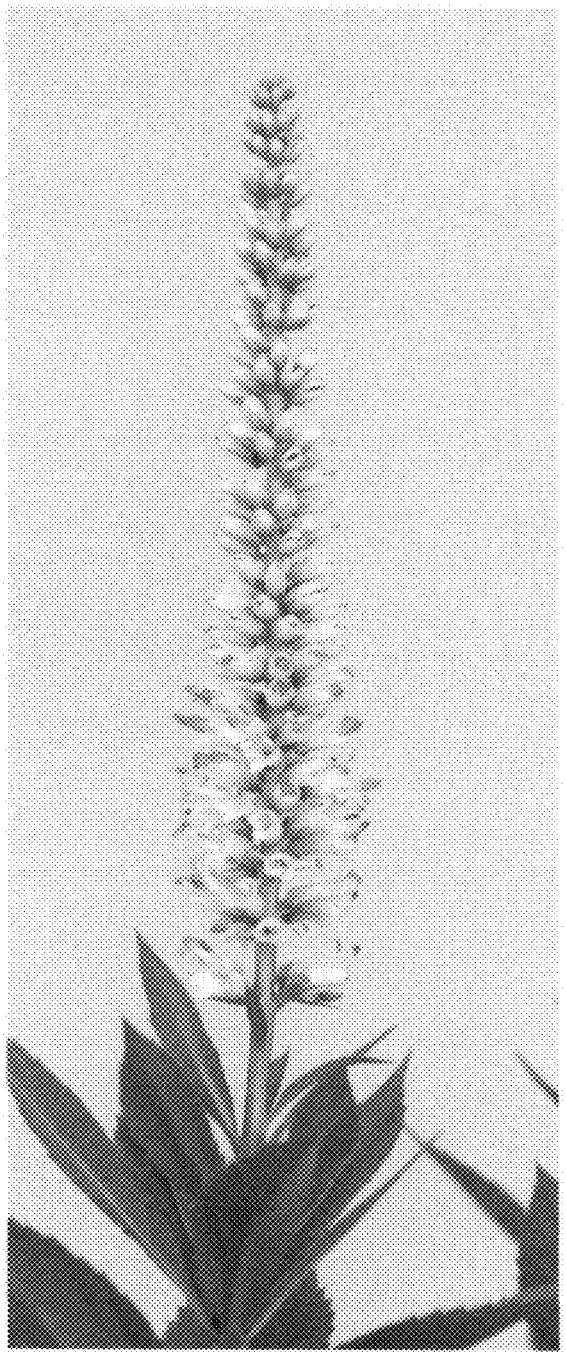

* * * * *